United States Patent
Ashmore et al.

(10) Patent No.: US 8,895,595 B2
(45) Date of Patent: Nov. 25, 2014

(54) MICROBICIDAL COMPOSITION

(71) Applicant: Rohm and Haas Company, Philadelphia, PA (US)

(72) Inventors: John W. Ashmore, Lansdale, PA (US); Beverly J. El A'mma, Perkiomenville, PA (US); Beat Heer, Grabs (CH); Kiran Pareek, Bensalem, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 14/150,034

(22) Filed: Jan. 8, 2014

(65) Prior Publication Data

US 2014/0121253 A1    May 1, 2014

Related U.S. Application Data

(62) Division of application No. 12/214,425, filed on Jun. 19, 2008, now Pat. No. 8,658,679.

(60) Provisional application No. 60/936,564, filed on Jun. 21, 2007.

(51) Int. Cl.
*A01N 43/80* (2006.01)
*A01N 43/653* (2006.01)
*A01N 37/34* (2006.01)

(52) U.S. Cl.
CPC .............. *A01N 43/80* (2013.01); *A01N 43/653* (2013.01); *A01N 37/34* (2013.01)
USPC ........................................... 514/373; 514/383

(58) Field of Classification Search
CPC ............................ A01N 43/80; A01N 43/653
See application file for complete search history.

(56) References Cited

U.S. PATENT DOCUMENTS

| | | | |
|---|---|---|---|
| 6,726,937 B2 * | 4/2004 | Imai | 424/635 |
| 2004/0198785 A1 | 10/2004 | Heer et al. | |
| 2005/0197366 A1 | 9/2005 | Chia et al. | |
| 2007/0078118 A1 | 4/2007 | Levy et al. | |

FOREIGN PATENT DOCUMENTS

GB    1531431 A    11/1978

* cited by examiner

*Primary Examiner* — David J Blanchard
*Assistant Examiner* — Peter Anthopolos
(74) *Attorney, Agent, or Firm* — Kenneth Crimaldi

(57) ABSTRACT

Synergistic microbicidal compositions containing N-methyl-1,2-benzisothiazolin-3-one.

1 Claim, No Drawings

MICROBICIDAL COMPOSITION

This invention relates to a synergistic combination of selected microbicides having greater activity than would be observed for the individual microbicides.

In some cases, commercial microbicides cannot provide effective control of microorganisms, even at high use concentrations, due to weak activity against certain types of microorganisms, e.g., those resistant to some microbicides, or due to aggressive environmental conditions. Combinations of different microbicides are sometimes used to provide overall control of microorganisms in a particular end use environment. For example, U.S. Pat. App. Pub. No. 2007/0078118 discloses synergistic combinations of N-methyl-1,2-benzisothiazolin-3-one (MBIT) with other biocides. However, there is a need for additional combinations of microbicides having enhanced activity against various strains of microorganisms to provide effective control of the microorganisms. Moreover, there is a need for combinations containing lower levels of individual microbicides for environmental and economic benefit. The problem addressed by this invention is to provide such additional combinations of microbicides.

STATEMENT OF THE INVENTION

The present invention is directed to a microbicidal composition comprising: (a) N-methyl-1,2-benzisothiazolin-3-one; and (b) at least one microbicide selected from among 2,2-dibromo-3-nitrilopropionamide, formaldehyde, 2-N-octyl-4-isothiazolin-3-one, propiconazole, tebuconazole, and a mixture of chloro-2-methyl-4-isothiazolin-3-one and 2-methyl-4-isothiazolin-3-one.

DETAILED DESCRIPTION OF THE INVENTION

As used herein, the following terms have the designated definitions, unless the context clearly indicates otherwise. "MBIT" is N-methyl-1,2-benzisothiazolin-3-one. The term "microbicide" refers to a compound capable of killing, inhibiting the growth of or controlling the growth of microorganisms at a locus; microbicides include bactericides, fungicides and algaecides. The term "microorganism" includes, for example, fungi (such as yeast and mold), bacteria and algae. The term "locus" refers to an industrial system or product subject to contamination by microorganisms. The following abbreviations are used throughout the specification: ppm=parts per million by weight (weight/weight), mL=milliliter, ATCC=American Type Culture Collection, MBC=minimum biocidal concentration, and MIC=minimum inhibitory concentration. Unless otherwise specified, temperatures are in degrees centigrade (° C.), and references to percentages (%) are by weight. Amounts of organic microbicides are given on an active ingredient basis in ppm (w/w).

The compositions of the present invention unexpectedly have been found to provide enhanced microbicidal efficacy at a combined active ingredient level lower than that of the individual microbicides.

In one embodiment of the invention, the antimicrobial composition comprises N-methyl-1,2-benzisothiazolin-3-one and 2,2-dibromo-3-nitrilopropionamide. Preferably, a weight ratio of 2,2-dibromo-3-nitrilopropionamide to N-methyl-1,2-benzisothiazolin-3-one is from 1:0.01 to 1:114, more preferably from 1:0.01 to 1:29, more preferably from 0.02 to 1:5.8.

In one embodiment of the invention, the antimicrobial composition comprises N-methyl-1,2-benzisothiazolin-3-one and formaldehyde. Preferably, a weight ratio of formaldehyde to N-methyl-1,2-benzisothiazolin-3-one is from 1:0.0022 to 1:19, more preferably from 1:0.022 to 1:19, more preferably from 1:0.17 to 1:19.

In one embodiment of the invention, the antimicrobial composition comprises N-methyl-1,2-benzisothiazolin-3-one and 2-N-octyl-4-isothiazolin-3-one. Preferably, a weight ratio of 2-N-octyl-4-isothiazolin-3-one to N-methyl-1,2-benzisothiazolin-3-one is from 1:0.02 to 1:882, more preferably from 1:0.13 to 1:882, more preferably from 1:0.13 to 1:150.

In one embodiment of the invention, the antimicrobial composition comprises N-methyl-1,2-benzisothiazolin-3-one and propiconazole. Preferably, a weight ratio of propiconazole to N-methyl-1,2-benzisothiazolin-3-one is from 1:0.0022 to 1:6.8, more preferably from 1:0.075 to 1:6.8.

In one embodiment of the invention, the antimicrobial composition comprises N-methyl-1,2-benzisothiazolin-3-one and tebuconazole. Preferably, a weight ratio of tebuconazole to N-methyl-1,2-benzisothiazolin-3-one is from 1:0.0033 to 1:46, more preferably from 1:0.15 to 1:46.

In one embodiment of the invention, the antimicrobial composition comprises N-methyl-1,2-benzisothiazolin-3-one and a 3:1 mixture of chloro-2-methyl-4-isothiazolin-3-one and 2-methyl-4-isothiazolin-3-one. Preferably, the mixture is about a 3:1 mixture, respectively. Preferably, a weight ratio of the mixture to N-methyl-1,2-benzisothiazolin-3-one is from 1:91 to 1:114.

The microbicides in the composition of this invention may be used "as is" or may first be formulated with a solvent or a solid carrier. Suitable solvents include, for example, water; glycols, such as ethylene glycol, propylene glycol, diethylene glycol, dipropylene glycol, polyethylene glycol, and polypropylene glycol; glycol ethers; alcohols, such as methanol, ethanol, propanol, phenethyl alcohol and phenoxypropanol; ketones, such as acetone and methyl ethyl ketone; esters, such as ethyl acetate, butyl acetate, triacetyl citrate, and glycerol triacetate; carbonates, such as propylene carbonate and dimethyl carbonate; and mixtures thereof. It is preferred that the solvent is selected from water, glycols, glycol ethers, esters and mixtures thereof. Suitable solid carriers include, for example, cyclodextrin, silicas, diatomaceous earth, waxes, cellulosic materials, alkali and alkaline earth (e.g., sodium, magnesium, potassium) metal salts (e.g., chloride, nitrate, bromide, sulfate) and charcoal.

When a microbicide component is formulated in a solvent, the formulation may optionally contain surfactants. When such formulations contain surfactants, they are generally in the form of emulsive concentrates, emulsions, microemulsive concentrates, or microemulsions. Emulsive concentrates form emulsions upon the addition of a sufficient amount of water. Microemulsive concentrates form microemulsions upon the addition of a sufficient amount of water. Such emulsive and microemulsive concentrates are generally well known in the art; it is preferred that such formulations are free of surfactants. U.S. Pat. No. 5,444,078 may be consulted for further general and specific details on the preparation of various microemulsions and microemulsive concentrates.

A microbicide component also can be formulated in the form of a dispersion. The solvent component of the dispersion can be an organic solvent or water, preferably water. Such dispersions can contain adjuvants, for example, co-solvents, thickeners, anti-freeze agents, dispersants, fillers, pigments, surfactants, biodispersants, sulfosuccinates, terpenes, furanones, polycations, stabilizers, scale inhibitors and anti-corrosion additives.

When both microbicides are each first formulated with a solvent, the solvent used for the first microbicide may be the same as or different from the solvent used to formulate the other commercial microbicide, although water is preferred for most industrial biocide applications. It is preferred that the two solvents are miscible.

Those skilled in the art will recognize that the microbicide components of the present invention may be added to a locus sequentially, simultaneously, or may be combined before being added to the locus. It is preferred that the first microbicide and the second microbicide component be added to a locus simultaneously or sequentially. When the microbicides are added simultaneously or sequentially, each individual component may contain adjuvants, such as, for example, solvent, thickeners, anti-freeze agents, colorants, sequestrants (such as ethylenediamine-tetraacetic acid, ethylenediaminedisuccinic acid, iminodisuccinic acid and salts thereof), dispersants, surfactants, biodispersants, sulfosuccinates, terpenes, furanones, polycations, stabilizers, scale inhibitors and anti-corrosion additives.

The microbicidal compositions of the present invention can be used to inhibit the growth of microorganisms or higher forms of aquatic life (such as protozoans, invertebrates, bryozoans, dinoflagellates, crustaceans, mollusks, etc.) by introducing a microbicidally effective amount of the compositions onto, into, or at a locus subject to microbial attack. Suitable loci include, for example: industrial process water; electrocoat deposition systems,; cooling towers; air washers; gas scrubbers; mineral slurries; wastewater treatment; ornamental fountains; reverse osmosis filtration; ultrafiltration; ballast water; evaporative condensers; heat exchangers; pulp and paper processing fluids and additives; starch; plastics; emulsions; dispersions; paints; latices; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household products, such as bathroom and kitchen cleaners; cosmetics; toiletries; shampoos; soaps; detergents; industrial cleaners; floor polishes; laundry rinse water; metalworking fluids; conveyor lubricants; hydraulic fluids; leather and leather products; textiles; textile products; wood and wood products, such as plywood, chipboard, wallboard, flakeboard, laminated beams, oriented strandboard, hardboard, and particleboard; petroleum processing fluids; fuel; oilfield fluids, such as injection water, fracture fluids, and drilling muds; agriculture adjuvant preservation; surfactant preservation; medical devices; diagnostic reagent preservation; food preservation, such as plastic or paper food wrap; food, beverage, and industrial process pasteurizers; toilet bowls; recreational water; pools; and spas.

Preferably, the microbicidal compositions of the present invention are used to inhibit the growth of microorganisms at a locus selected from one or more of mineral slurries, pulp and paper processing fluids and additives, starch, emulsions, dispersions, paints, latices, coatings, construction adhesives, such as ceramic adhesives, carpet backing adhesives, photographic chemicals, printing fluids, household products such as bathroom and kitchen cleaners, cosmetics, toiletries, shampoos, soaps, detergents, industrial cleaners, floor polishes, laundry rinse water, metal working fluids, textile products, wood and wood products, agriculture adjuvant preservation, surfactant preservation, diagnostic reagent preservation, food preservation, and food, beverage, and industrial process pasteurizers.

The specific amount of the composition of this invention necessary to inhibit or control the growth of microorganisms and higher aquatic life forms in a locus depends upon the particular locus to be protected. Typically, the amount of the composition of the present invention to control the growth of microorganisms in a locus is sufficient if it provides from 0.1 to 1,000 ppm of the isothiazoline ingredient of the composition in the locus. It is preferred that the isothiazolone ingredients of the composition be present in the locus in an amount of at least 0.5 ppm, more preferably at least 4 ppm and most preferably at least 10 ppm. It is preferred that the isothiazolone ingredients of the composition be present in the locus in an amount of no more than 1000 ppm, more preferably no more than 500 ppm, and most preferably no more than 200 ppm.

EXAMPLES

Materials and Methods

The synergism of the combination of the present invention was demonstrated by testing a wide range of concentrations and ratios of the compounds.

One measure of synergism is the industrially accepted method described by Kull, F. C.; Eisman, P. C.; Sylwestrowicz, H. D. and Mayer, R. L., in *Applied Microbiology* 9:538-541 (1961), using the ratio determined by the formula:

$$Q_a/Q_A + Q_b/Q_B = \text{Synergy Index("SI")}$$

wherein:
$Q_A$=concentration of compound A (first component) in ppm, acting alone, which produced an end point (MIC of Compound A).
$Q_a$=concentration of compound A in ppm, in the mixture, which produced an end point.
$Q_B$=concentration of compound B (second component) in ppm, acting alone, which produced an end point (MIC of Compound B).
$Q_b$=concentration of compound B in ppm, in the mixture, which produced an end point.

When the sum of $Q_a/Q_A$ and $Q_b/Q_B$ is greater than one, antagonism is indicated. When the sum is equal to one, additivity is indicated, and when less than one, synergism is demonstrated. The lower the SI, the greater the synergy shown by that particular mixture. The minimum inhibitory concentration (MIC) of a microbicide is the lowest concentration tested under a specific set of conditions that prevents the growth of added microorganisms.

Synergy tests were conducted using standard microtiter plate assays with media designed for optimal growth of the test microorganism. Minimal salt medium supplemented with 0.2% glucose and 0.1% yeast extract (M9GY medium) was used for testing bacteria; Potato Dextrose Broth (PDB medium) was used for testing yeast and mold. In this method, a wide range of combinations of microbicides was tested by conducting high resolution MIC assays in the presence of various concentrations of MBIT. High resolution MICs were determined by adding varying amounts of microbicide to one column of a microtitre plate and doing subsequent ten-fold dilutions using an automated liquid handling system to obtain a series of endpoints ranging from 2 ppm to 10,000 ppm active ingredient.

The synergy of the combinations of the present invention was determined against a bacterium, *Escherichia coli* (*E. coli*—ATCC #8739), a yeast, *Candida albicans* (*C. albicans*—ATCC 10231), and a mold, *Aspergillus niger* (*A. niger*—ATCC 16404). The bacteria were used at a concentration of about $5\times10^6$ bacteria per mL and the yeast and mold at $5\times10^5$ fungi per mL. These microorganisms are representative of natural contaminants in many consumer and industrial applications. The plates were visually evaluated for microbial growth (turbidity) to determine the MIC after various incubation times at 25° C. (yeast and mold) or 30° C. (bacteria).

The test results for demonstration of synergy of the MBIT combinations of the present invention are shown below in Tables 1 through 6. In each test, Second Component (B) was MBIT and the First Component (A) was the other commercial microbicide. Each table shows the specific combinations of MBIT and the other component; results against the microorganisms tested with incubation times; the end-point activity in ppm measured by the MIC for MBIT alone ($Q_B$), for the other component alone ($Q_A$), for MBIT in the mixture ($Q_b$) and for the other component in the mixture ($Q_a$); the calculated SI value; and the range of synergistic ratios for each combination tested (other component/MBIT or A/B).

TABLE 1

| Test Organisms | Contact Time | Ca | Cb | S.I. | Ca:Cb |
|---|---|---|---|---|---|
| A. niger ATCC #16404 | 3 days | 1.275 | — | — | — |
| | | — | 150 | — | — |
| | | 0.6 | 75 | 0.97 | 1:125.0000 |
| | | 0.9 | 75 | 1.21 | 1:83.3333 |
| | | 0.9 | 1.2 | 0.71 | 1:1.3333 |
| | | 1.275 | 1.2 | 1.01 | 1:0.9412 |
| C. albicans ATCC #10231 | 48 hrs | 1.275 | — | — | — |
| | | — | 30 | — | — |
| | | 1.275 | 1.86 | 1.06 | 1:1.4588 |
| | | 1.275 | 0.94 | 1.03 | 1:0.7373 |
| | 72 hrs | 1.275 | — | — | — |
| | | — | 30 | — | — |
| | | 1.275 | 1.86 | 1.06 | 1:1.4588 |
| | | 1.275 | 0.94 | 1.03 | 1:0.7373 |
| Ps. aeruginosa ATCC #9027 | 24 hrs | 1.275 | — | — | — |
| | | — | 100 | — | — |
| | | 1.275 | 6 | 1.06 | 1:4.7059 |
| | 48 hrs | 1.275 | — | — | — |
| | | — | 175 | — | — |
| | | 0.6 | 100 | 1.04 | 1:166.6667 |
| S. aureus ATCC #6538 | 48 hrs | 0.9 | — | — | — |
| | | — | 60 | — | — |
| | | 0.2625 | 30 | 0.79 | 1:114.2857 |
| | | 0.33 | 30 | 0.87 | 1:90.9091 |
| | | 0.6 | 30 | 1.17 | 1:50.0000 |

Ca—ppm AI of CMI/MI (Chloro-2-methyl-4-isothiazolin-3-one/2-Methyl-4-isothiazolin-3-one)
Cb—ppm AI of MBIT (N-methyl-1,2-benzisothiazolin-3-one)
Ratio: Ca:Cb

TABLE 2

| Test Organisms | Contact Time | Ca | Cb | S.I. | Ca:Cb |
|---|---|---|---|---|---|
| A. niger ATCC #16404 | 3 days | 42.5 | — | — | — |
| | | — | 9.4 | — | — |
| | | 4.25 | 4.7 | 0.60 | 1:1.1059 |
| | | 5.25 | 4.7 | 0.62 | 1:0.8952 |
| | | 8.75 | 4.7 | 0.71 | 1:0.5371 |
| | | 11 | 4.7 | 0.76 | 1:0.4273 |
| | | 20 | 4.7 | 0.97 | 1:0.2350 |
| | | 30 | 4.7 | 1.21 | 1:0.1567 |
| | | 4.25 | 2.4 | 0.36 | 1:0.5647 |
| | | 5.25 | 2.4 | 0.38 | 1:0.4571 |
| | | 8.75 | 2.4 | 0.46 | 1:0.2743 |
| | | 11 | 2.4 | 0.51 | 1:0.2182 |
| | | 20 | 2.4 | 0.73 | 1:0.1200 |
| | | 30 | 2.4 | 0.96 | 1:0.0800 |
| | | 42.5 | 2.4 | 1.26 | 1:0.0565 |
| | | 4.25 | 1.2 | 0.23 | 1:0.2824 |
| | | 5.25 | 1.2 | 0.25 | 1:0.2286 |
| | | 8.75 | 1.2 | 0.33 | 1:0.1371 |
| | | 11 | 1.2 | 0.39 | 1:0.1091 |
| | | 20 | 1.2 | 0.60 | 1:0.0600 |

TABLE 2-continued

| Test Organisms | Contact Time | Ca | Cb | S.I. | Ca:Cb |
|---|---|---|---|---|---|
| | | 30 | 1.2 | 0.83 | 1:0.0400 |
| | | 42.5 | 1.2 | 1.13 | 1:0.0282 |
| | 7 days | 200 | — | — | — |
| | | — | 18.8 | — | — |
| | | 42.5 | 9.4 | 0.71 | 1:0.2212 |
| | | 52.5 | 9.4 | 0.76 | 1:0.1790 |
| | | 65 | 9.4 | 0.83 | 1:0.1446 |
| | | 87.5 | 9.4 | 0.94 | 1:0.1074 |
| | | 110 | 9.4 | 1.05 | 1:0.0855 |
| | | 87.5 | 4.7 | 0.69 | 1:0.0537 |
| | | 110 | 4.7 | 0.80 | 1:0.0427 |
| | | 200 | 4.7 | 1.25 | 1:0.0235 |
| | | 65 | 2.4 | 0.45 | 1:0.0369 |
| | | 87.5 | 2.4 | 0.57 | 1:0.0274 |
| | | 110 | 2.4 | 0.68 | 1:0.0218 |
| | | 200 | 2.4 | 1.13 | 1:0.0120 |
| | | 87.5 | 1.2 | 0.50 | 1:0.0137 |
| | | 110 | 1.2 | 0.61 | 1:0.0109 |
| | | 200 | 1.2 | 1.06 | 1:0.0060 |
| C. albicans ATCC #10231 | 48 hrs | 44 | — | — | — |
| | | — | 30 | — | — |
| | | 2.6 | 15 | 0.56 | 1:5.7692 |
| | | 4.4 | 15 | 0.60 | 1:3.4091 |
| | | 8 | 15 | 0.68 | 1:1.8750 |
| | | 12 | 15 | 0.77 | 1:1.2500 |
| | | 17 | 15 | 0.89 | 1:0.8824 |
| | | 21 | 15 | 0.98 | 1:0.7143 |
| | | 26 | 15 | 1.09 | 1:0.5769 |
| | | 8 | 7.5 | 0.43 | 1:0.9375 |
| | | 12 | 7.5 | 0.52 | 1:0.6250 |
| | | 17 | 7.5 | 0.64 | 1:0.4412 |
| | | 21 | 7.5 | 0.73 | 1:0.3571 |
| | | 26 | 7.5 | 0.84 | 1:0.2885 |
| | | 44 | 7.5 | 1.13 | 1:0.1705 |
| | | 44 | 3.75 | 1.06 | 1:0.0852 |
| | | 35 | 1.86 | 0.86 | 1:0.0531 |
| | | 44 | 1.86 | 1.03 | 1:0.0423 |
| | | 44 | 0.94 | 1.03 | 1:0.0214 |
| | 72 hrs | >44 | — | — | — |
| | | — | 30 | — | — |
| | | 4.4 | 15 | 0.6 | 1:3.4091 |
| | | 8 | 15 | 0.68 | 1:1.8750 |
| | | 12 | 15 | 0.77 | 1:1.2500 |
| | | 17 | 15 | 0.89 | 1:0.8824 |
| | | 21 | 15 | 0.98 | 1:0.7143 |
| | | 26 | 15 | 1.09 | 1:0.5769 |
| | | 8 | 7.5 | 0.43 | 1:0.9375 |
| | | 12 | 7.5 | 0.52 | 1:0.6250 |
| | | 17 | 7.5 | 0.64 | 1:0.4412 |
| | | 21 | 7.5 | 0.73 | 1:0.3571 |
| | | 26 | 7.5 | 0.84 | 1:0.2885 |
| | | 44 | 7.5 | 1.25 | 1:0.1705 |
| | | 35 | 1.86 | 0.86 | 1:0.0531 |
| | | 44 | 1.86 | 1.06 | 1:0.0423 |
| | | 44 | 0.94 | 1.03 | 1:0.0214 |
| Ps. Aeruginosa ATCC #9027 | 24 hrs | 4.25 | — | — | — |
| | | — | 100 | — | — |
| | | 2 | 50 | 0.97 | 1:25.0000 |
| | | 3 | 50 | 1.21 | 1:16.6667 |
| | | 3 | 25 | 0.96 | 1:8.3333 |
| | | 4.25 | 25 | 1.25 | 1:5.8824 |
| | | 4.25 | 6 | 1.06 | 1:1.4118 |
| | 48 hrs | 5.25 | — | — | — |
| | | — | 175 | — | — |
| | | 0.875 | 100 | 0.74 | 1:114.2857 |
| | | 1.1 | 100 | 0.78 | 1:90.9091 |
| | | 2 | 100 | 0.95 | 1:50.0000 |
| | | 3 | 100 | 1.14 | 1:33.3333 |
| | | 5.25 | 12 | 1.07 | 1:2.2857 |
| S. aureus ATCC #6538 | 48 hrs | 8.5 | — | — | — |
| | | — | 60 | — | — |
| | | 1.05 | 30 | 0.62 | 1:28.5714 |
| | | 4 | 30 | 0.97 | 1:7.5000 |
| | | 6 | 30 | 1.21 | 1:5.0000 |
| | | 4 | 15 | 0.72 | 1:3.7500 |
| | | 6 | 15 | 0.96 | 1:2.5000 |
| | | 8.5 | 15 | 1.25 | 1:1.7647 |

TABLE 2-continued

| Test Organisms | Contact Time | Ca | Cb | S.I. | Ca:Cb |
|---|---|---|---|---|---|
| | | 6 | 2 | 0.74 | 1:0.3333 |
| | | 8.5 | 2 | 1.03 | 1:0.2353 |
| | | 6 | 1 | 0.72 | 1:0.1667 |
| | | 8.5 | 1 | 1.02 | 1:0.1176 |

Ca—ppm AI of DBNPA (2,2-Dibromo-3-nitrilopropionamide)
Cb—ppm AI of MBIT(N-methyl-1,2-benzisothiazolin-3-one)
Ratio: Ca:Cb

TABLE 3

| Test Organisms | Contact Time | Ca | Cb | S.I. | Ca:Cb |
|---|---|---|---|---|---|
| A. niger ATCC #16404 | 3 days | 200 | — | — | — |
| | | — | 75 | — | — |
| | | 2 | 37.5 | 0.51 | 1:18.7500 |
| | | 5.25 | 37.5 | 0.53 | 1:7.1429 |
| | | 8.75 | 37.5 | 0.54 | 1:4.2857 |
| | | 11 | 37.5 | 0.56 | 1:3.4091 |
| | | 20 | 37.5 | 0.60 | 1:1.8750 |
| | | 30 | 37.5 | 0.65 | 1:1.2500 |
| | | 42.5 | 37.5 | 0.71 | 1:0.8824 |
| | | 52.5 | 37.5 | 0.76 | 1:0.7143 |
| | | 65 | 37.5 | 0.83 | 1:0.5769 |
| | | 87.5 | 37.5 | 0.94 | 1:0.4286 |
| | | 110 | 37.5 | 1.05 | 1:0.3409 |
| | | 42.5 | 18.8 | 0.46 | 1:0.4424 |
| | | 52.5 | 18.8 | 0.51 | 1:0.3581 |
| | | 65 | 18.8 | 0.58 | 1:0.2892 |
| | | 87.5 | 18.8 | 0.69 | 1:0.2149 |
| | | 110 | 18.8 | 0.80 | 1:0.1709 |
| | | 200 | 18.8 | 1.25 | 1:0.0940 |
| | | 65 | 9.4 | 0.45 | 1:0.1446 |
| | | 87.5 | 9.4 | 0.56 | 1:0.1074 |
| | | 110 | 9.4 | 0.68 | 1:0.0855 |
| | | 200 | 9.4 | 1.13 | 1:0.0470 |
| | | 87.5 | 4.7 | 0.50 | 1:0.0537 |
| | | 110 | 4.7 | 0.61 | 1:0.0427 |
| | | 200 | 4.7 | 1.06 | 1:0.0235 |
| | | 110 | 2.4 | 0.58 | 1:0.0218 |
| | | 200 | 2.4 | 1.03 | 1:0.0120 |
| | | 200 | 1.2 | 1.02 | 1:0.0060 |
| | 7 days | 425 | — | — | — |
| | | — | 150 | — | — |
| | | 65 | 75 | 0.65 | 1:1.1538 |
| | | 87.5 | 75 | 0.71 | 1:0.8571 |
| | | 110 | 75 | 0.76 | 1:0.6818 |
| | | 200 | 75 | 0.97 | 1:0.3750 |
| | | 300 | 75 | 1.21 | 1:0.2500 |
| | | 300 | 37.5 | 0.96 | 1:0.1250 |
| | | 425 | 37.5 | 1.25 | 1:0.0882 |
| | | 200 | 18.8 | 0.6 | 1:0.0940 |
| | | 300 | 18.8 | 0.83 | 1:0.0627 |
| | | 425 | 18.8 | 1.13 | 1:0.0442 |
| | | 425 | 9.4 | 1.06 | 1:0.0221 |
| | | 425 | 4.7 | 1.03 | 1:0.0111 |
| | | 300 | 2.4 | 0.72 | 1:0.0080 |
| | | 425 | 2.4 | 1.02 | 1:0.0056 |
| | | 300 | 1.2 | 0.71 | 1:0.0040 |
| | | 425 | 1.2 | 1.01 | 1:0.0028 |
| C. albicans ATCC #10231 | 48 hrs | 425 | — | — | — |
| | | — | 30 | — | — |
| | | 87.5 | 15 | 0.71 | 1:0.1714 |
| | | 110 | 15 | 0.76 | 1:0.1364 |
| | | 200 | 15 | 0.97 | 1:0.0750 |
| | | 300 | 15 | 1.21 | 1:0.0500 |
| | | 875 | 7.5 | 2.31 | 1:0.0086 |
| | | 300 | 3.75 | 0.83 | 1:0.0125 |
| | | 425 | 3.75 | 1.13 | 1:0.0088 |
| | | 300 | 1.86 | 0.77 | 1:0.0062 |
| | | 425 | 1.86 | 1.06 | 1:0.0044 |
| | | 425 | 0.94 | 1.03 | 1:0.0022 |
| | 72 hrs | 525 | — | — | — |
| | | — | 30 | — | — |

TABLE 3-continued

| Test Organisms | Contact Time | Ca | Cb | S.I. | Ca:Cb |
|---|---|---|---|---|---|
| | | 110 | 15 | 0.71 | 1:0.1364 |
| | | 200 | 15 | 0.88 | 1:0.0750 |
| | | 300 | 15 | 1.07 | 1:0.0500 |
| | | 300 | 3.75 | 0.70 | 1:0.0125 |
| | | 425 | 3.75 | 0.93 | 1:0.0088 |
| | | 525 | 3.75 | 1.13 | 1:0.0071 |
| | | 425 | 1.86 | 0.87 | 1:0.0044 |
| | | 525 | 1.86 | 1.06 | 1:0.0035 |
| | | 425 | 0.94 | 0.84 | 1:0.0022 |
| | | 525 | 0.94 | 1.03 | 1:0.0018 |
| Ps. aeruginosa ATCC #9027 | 24 hrs | 15 | — | — | — |
| | | — | 100 | — | — |
| | | 15 | 6 | 1.06 | 1:0.4000 |
| | 48 hrs | 26.25 | — | — | — |
| | | — | 175 | — | — |
| | | 10 | 100 | 0.95 | 1:10.0000 |
| | | 15 | 100 | 1.14 | 1:6.6667 |
| | | 15 | 50 | 0.86 | 1:3.3333 |
| | | 21.25 | 50 | 1.10 | 1:2.3529 |
| | | 21.25 | 25 | 0.95 | 1:1.1765 |
| | | 26.25 | 25 | 1.14 | 1:0.9524 |
| | | 21.25 | 12 | 0.88 | 1:0.5647 |
| | | 26.25 | 12 | 1.07 | 1:0.4571 |
| | | 21.25 | 6 | 0.84 | 1:0.2824 |
| | | 26.25 | 6 | 1.03 | 1:0.2286 |
| S. aureus ATCC #6538 | 24 hrs | 30 | — | — | — |
| | | — | 60 | — | — |
| | | 3 | 30 | 0.60 | 1:10.0000 |
| | | 5.25 | 30 | 0.68 | 1:5.7143 |
| | | 11 | 30 | 0.87 | 1:2.7273 |
| | | 20 | 30 | 1.17 | 1:1.5000 |
| | | 20 | 15 | 0.92 | 1:0.7500 |
| | | 30 | 15 | 1.25 | 1:0.5000 |
| | | 30 | 3 | 1.05 | 1:0.1000 |
| | | 30 | 2 | 1.03 | 1:0.0667 |
| | | 30 | 1 | 1.02 | 1:0.0333 |
| | 48 hrs | 30 | — | — | — |
| | | — | 60 | — | — |
| | | 5.25 | 30 | 0.68 | 1:5.7143 |
| | | 11 | 30 | 0.87 | 1:2.7273 |
| | | 20 | 30 | 1.17 | 1:1.5000 |
| | | 20 | 15 | 0.92 | 1:0.7500 |
| | | 30 | 3 | 1.05 | 1:0.1000 |
| | | 30 | 2 | 1.03 | 1:0.0667 |
| | | 30 | 1 | 1.02 | 1:0.0333 |

Ca—ppm AI of HCHO (Formaldehyde)
Cb—ppm AI of MBIT(N-methyl-1,2-benzisothiazolin-3-one)
Ratio: Ca:Cb

TABLE 4

| Test Organisms | Contact Time | Ca | Cb | S.I. | Ca:Cb |
|---|---|---|---|---|---|
| A. niger ATCC #16404 | 3 days | 0.65 | — | — | — |
| | | — | 75 | — | — |
| | | 0.0425 | 37.5 | 0.57 | 1:882.3529 |
| | | 0.065 | 37.5 | 0.60 | 1:576.9231 |
| | | 0.11 | 37.5 | 0.67 | 1:340.9091 |
| | | 0.2 | 37.5 | 0.81 | 1:187.5000 |
| | | 0.3 | 37.5 | 0.96 | 1:125.0000 |
| | | 0.425 | 37.5 | 1.15 | 1:88.2353 |
| | | 0.525 | 18.8 | 1.06 | 1:35.8095 |
| | | 0.525 | 9.4 | 0.93 | 1:17.9048 |
| | | 0.65 | 9.4 | 1.13 | 1:14.4615 |
| | | 0.525 | 4.7 | 0.87 | 1:8.9524 |
| | | 0.65 | 4.7 | 1.06 | 1:7.2308 |
| | | 0.65 | 2.4 | 1.03 | 1:3.6923 |
| | | 0.65 | 1.2 | 1.02 | 1:1.8462 |
| | 7 days | 8.75 | — | — | — |
| | | — | 150 | — | — |
| | | 0.525 | 150 | 1.06 | 1:285.7143 |
| | | 1.1 | 75 | 0.63 | 1:68.1818 |
| | | 2 | 75 | 0.73 | 1:37.5000 |

TABLE 4-continued

| Test Organisms | Contact Time | Ca | Cb | S.I. | Ca:Cb |
|---|---|---|---|---|---|
| | | 3 | 75 | 0.84 | 1:25.0000 |
| | | 4.25 | 75 | 0.99 | 1:17.6471 |
| | | 5.25 | 75 | 1.10 | 1:14.2857 |
| | | 2 | 37.5 | 0.48 | 1:18.7500 |
| | | 3 | 37.5 | 0.59 | 1:12.5000 |
| | | 4.25 | 37.5 | 0.74 | 1:8.8235 |
| | | 5.25 | 37.5 | 0.85 | 1:7.1429 |
| | | 6.5 | 37.5 | 0.99 | 1:5.7692 |
| | | 8.75 | 37.5 | 1.25 | 1:4.2857 |
| | | 0.875 | 18.8 | 0.23 | 1:21.4857 |
| | | 1.1 | 18.8 | 0.25 | 1:17.0909 |
| | | 2 | 18.8 | 0.35 | 1:9.4000 |
| | | 3 | 18.8 | 0.47 | 1:6.2667 |
| | | 4.25 | 18.8 | 0.61 | 1:4.4235 |
| | | 6.5 | 18.8 | 0.87 | 1:2.8923 |
| | | 8.75 | 18.8 | 1.13 | 1:2.1486 |
| | | 2 | 9.4 | 0.29 | 1:4.7000 |
| | | 3 | 9.4 | 0.41 | 1:3.1333 |
| | | 4.25 | 9.4 | 0.55 | 1:2.2118 |
| | | 5.25 | 9.4 | 0.66 | 1:1.7905 |
| | | 6.5 | 9.4 | 0.81 | 1:1.4462 |
| | | 8.75 | 9.4 | 1.06 | 1:1.0743 |
| | | 2 | 4.7 | 0.26 | 1:2.3500 |
| | | 3 | 4.7 | 0.37 | 1:1.5667 |
| | | 4.25 | 4.7 | 0.52 | 1:1.1059 |
| | | 5.25 | 4.7 | 0.63 | 1:0.8952 |
| | | 6.5 | 4.7 | 0.77 | 1:0.7231 |
| | | 8.75 | 4.7 | 1.03 | 1:0.5371 |
| | | 5.25 | 2.4 | 0.62 | 1:0.4571 |
| | | 6.5 | 2.4 | 0.76 | 1:0.3692 |
| | | 8.75 | 2.4 | 1.02 | 1:0.2743 |
| | | 5.25 | 1.2 | 0.61 | 1:0.2286 |
| | | 6.5 | 1.2 | 0.75 | 1:0.1846 |
| | | 8.75 | 1.2 | 1.01 | 1:0.1371 |
| C. albicans ATCC #10231 | 48 hrs | 3.25 | — | — | — |
| | | — | 30 | — | — |
| | | 2.625 | 7.5 | 1.06 | 1:2.8571 |
| | | 2.625 | 3.75 | 0.93 | 1:1.4286 |
| | | 3.25 | 3.75 | 1.13 | 1:1.1538 |
| | | 3.25 | 1.86 | 1.06 | 1:0.5723 |
| | | 3.25 | 0.94 | 1.03 | 1:0.2892 |
| | 72 hrs | 3.25 | — | — | — |
| | | — | 30 | — | — |
| | | 3.25 | 1.86 | 1.06 | 1:0.5723 |
| | | 3.25 | 0.94 | 1.03 | 1:0.2892 |
| Ps. aeruginosa ATCC #9027 | 24 hrs | 650 | — | — | — |
| | | — | 100 | — | — |
| | | 525 | 25 | 1.06 | 1:0.0476 |
| | | 525 | 12 | 0.93 | 1:0.0229 |
| | | 650 | 12 | 1.12 | 1:0.0185 |
| | | 650 | 6 | 1.06 | 1:0.0092 |
| | 48 hrs | 650 | — | — | — |
| | | — | 175 | — | — |
| | | 200 | 100 | 0.88 | 1:0.5000 |
| | | 300 | 100 | 1.03 | 1:0.3333 |
| | | 525 | 50 | 1.09 | 1:0.0952 |
| | | 525 | 25 | 0.95 | 1:0.0476 |
| | | 650 | 25 | 1.14 | 1:0.0385 |
| | | 650 | 12 | 1.07 | 1:0.0185 |
| | | 650 | 6 | 1.03 | 1:0.0092 |
| S. aureus ATCC #6538 | 24 hrs | 30 | — | — | — |
| | | — | 30 | — | — |
| | | 3 | 15 | 0.60 | 1:5.0000 |
| | | 5.25 | 15 | 0.68 | 1:2.8571 |
| | | 6.5 | 15 | 0.72 | 1:2.3077 |
| | | 8.75 | 15 | 0.79 | 1:1.7143 |
| | | 11 | 15 | 0.87 | 1:1.3636 |
| | | 20 | 15 | 1.17 | 1:0.7500 |
| | | 20 | 7.5 | 0.92 | 1:0.3750 |
| | | 30 | 7.5 | 1.25 | 1:0.2500 |
| | | 30 | 2 | 1.07 | 1:0.0667 |
| | | 30 | 1 | 1.03 | 1:0.0333 |
| | 48 hrs | 200 | — | — | — |
| | | — | 60 | — | — |
| | | 0.2 | 30 | 0.50 | 1:150.0000 |
| | | 2 | 30 | 0.51 | 1:15.0000 |
| | | 20 | 30 | 0.60 | 1:1.5000 |
| | | 30 | 30 | 0.65 | 1:1.0000 |
| | | 42.5 | 30 | 0.71 | 1:0.7059 |
| | | 52.5 | 30 | 0.76 | 1:0.5714 |
| | | 87.5 | 30 | 0.94 | 1:0.3429 |
| | | 110 | 30 | 1.05 | 1:0.2727 |
| | | 4.25 | 15 | 0.27 | 1:3.5294 |
| | | 2 | 15 | 0.26 | 1:7.5000 |
| | | 20 | 15 | 0.35 | 1:0.7500 |
| | | 30 | 15 | 0.40 | 1:0.5000 |
| | | 42.5 | 15 | 0.46 | 1:0.3529 |
| | | 52.5 | 15 | 0.51 | 1:0.2857 |
| | | 87.5 | 15 | 0.69 | 1:0.1714 |
| | | 110 | 15 | 0.80 | 1:0.1364 |
| | | 200 | 15 | 1.25 | 1:0.0750 |
| | | 20 | 7.5 | 0.23 | 1:0.3750 |
| | | 30 | 7.5 | 0.28 | 1:0.2500 |
| | | 42.5 | 7.5 | 0.34 | 1:0.1765 |
| | | 52.5 | 7.5 | 0.39 | 1:0.1429 |
| | | 87.5 | 7.5 | 0.56 | 1:0.0857 |
| | | 110 | 7.5 | 0.68 | 1:0.0682 |
| | | 200 | 7.5 | 1.13 | 1:0.0375 |
| | | 87.5 | 3 | 0.49 | 1:0.0343 |
| | | 110 | 3 | 0.6 | 1:0.0273 |
| | | 200 | 3 | 1.05 | 1:0.0150 |
| | | 200 | 2 | 1.03 | 1:0.0100 |
| | | 200 | 1 | 1.02 | 1:0.0050 |

Ca—ppm AI of OIT (2-N-octyl-4-isothiazolin-3-one)
Cb—ppm AI of MBIT(N-methyl-1,2-benzisothiazolin-3-one)
Ratio: Ca:Cb

TABLE 5

| Test Organisms | Contact Time | Ca | Cb | S.I. | Ca:Cb |
|---|---|---|---|---|---|
| A. niger ATCC #16404 | 3 days | 52.5 | — | — | — |
| | | — | 37.5 | — | — |
| | | 6.5 | 18.8 | 0.63 | 1:2.8923 |
| | | 11 | 18.8 | 0.71 | 1:1.7091 |
| | | 20 | 18.8 | 0.88 | 1:0.9400 |
| | | 30 | 18.8 | 1.07 | 1:0.6267 |
| | | 52.5 | 2.4 | 1.06 | 1:0.0457 |
| | | 52.5 | 1.2 | 1.03 | 1:0.0229 |
| | 7 days | 87.5 | — | — | — |
| | | — | 150 | — | — |
| | | 11 | 75 | 0.63 | 1:6.8182 |
| | | 20 | 75 | 0.73 | 1:3.7500 |
| | | 30 | 75 | 0.84 | 1:2.5000 |
| | | 42.5 | 75 | 0.99 | 1:1.7647 |
| | | 52.5 | 75 | 1.10 | 1:1.4286 |
| | | 42.5 | 37.5 | 0.74 | 1:0.8824 |
| | | 52.5 | 37.5 | 0.85 | 1:0.7143 |
| | | 65 | 37.5 | 0.99 | 1:0.5769 |
| | | 52.5 | 18.8 | 0.73 | 1:0.3581 |
| | | 65 | 18.8 | 0.87 | 1:0.2892 |
| | | 87.5 | 18.8 | 1.13 | 1:0.2149 |
| | | 87.5 | 9.6 | 1.06 | 1:0.1097 |
| | | 87.5 | 4.7 | 1.03 | 1:0.0537 |
| | | 87.5 | 2.4 | 1.02 | 1:0.0274 |
| | | 87.5 | 1.2 | 1.01 | 1:0.0137 |
| C. albicans ATCC #10231 | 48 hrs | 525 | — | — | — |
| | | — | 30 | — | — |
| | | 8.75 | 15 | 0.52 | 1:1.7143 |
| | | 20 | 15 | 0.54 | 1:0.7500 |
| | | 42.5 | 15 | 0.58 | 1:0.3529 |
| | | 65 | 15 | 0.62 | 1:0.2308 |
| | | 110 | 15 | 0.71 | 1:0.1364 |
| | | 200 | 15 | 0.88 | 1:0.0750 |
| | | 300 | 15 | 1.07 | 1:0.0500 |
| | | 65 | 7.5 | 0.37 | 1:0.1154 |
| | | 110 | 7.5 | 0.46 | 1:0.0682 |
| | | 200 | 7.5 | 0.63 | 1:0.0375 |
| | | 300 | 7.5 | 0.82 | 1:0.0250 |
| | | 425 | 7.5 | 1.06 | 1:0.0176 |

TABLE 5-continued

| Test Organisms | Contact Time | Ca | Cb | S.I. | Ca:Cb |
|---|---|---|---|---|---|
| | | 200 | 3.75 | 0.51 | 1:0.0188 |
| | | 300 | 3.75 | 0.70 | 1:0.0125 |
| | | 425 | 3.75 | 0.93 | 1:0.0088 |
| | | 525 | 3.75 | 1.13 | 1:0.0071 |
| | | 200 | 1.86 | 0.44 | 1:0.0093 |
| | | 300 | 1.86 | 0.63 | 1:0.0062 |
| | | 425 | 1.86 | 0.87 | 1:0.0044 |
| | | 525 | 1.86 | 1.06 | 1:0.0035 |
| | | 425 | 0.94 | 0.84 | 1:0.0022 |
| | | 525 | 0.94 | 1.03 | 1:0.0018 |
| | 72 hrs | 525 | — | — | — |
| | | — | 30 | — | — |
| | | 8.75 | 15 | 0.52 | 1:1.7143 |
| | | 20 | 15 | 0.54 | 1:0.7500 |
| | | 42.5 | 15 | 0.58 | 1:0.3529 |
| | | 65 | 15 | 0.62 | 1:0.2308 |
| | | 110 | 15 | 0.71 | 1:0.1364 |
| | | 200 | 15 | 0.88 | 1:0.0750 |
| | | 300 | 15 | 1.07 | 1:0.0500 |
| | | 65 | 7.5 | 0.37 | 1:0.1154 |
| | | 110 | 7.5 | 0.46 | 1:0.0682 |
| | | 200 | 7.5 | 0.63 | 1:0.0375 |
| | | 300 | 7.5 | 0.82 | 1:0.0250 |
| | | 425 | 7.5 | 1.06 | 1:0.0176 |
| | | 200 | 3.75 | 0.51 | 1:0.0188 |
| | | 300 | 3.75 | 0.70 | 1:0.0125 |
| | | 425 | 3.75 | 0.93 | 1:0.0088 |
| | | 525 | 3.75 | 1.13 | 1:0.0071 |
| | | 200 | 1.86 | 0.44 | 1:0.0093 |
| | | 300 | 1.86 | 0.63 | 1:0.0062 |
| | | 425 | 1.86 | 0.87 | 1:0.0044 |
| | | 525 | 1.86 | 1.06 | 1:0.0035 |
| | | 425 | 0.94 | 0.84 | 1:0.0022 |
| | | 525 | 0.94 | 1.03 | 1:0.0018 |
| Ps. Aeruginosa ATCC #9027 | 24 hrs | 875 | — | — | — |
| | | — | 100 | — | — |
| | | 650 | 25 | 0.99 | 1:0.0385 |
| | | 875 | 6 | 1.06 | 1:0.0069 |
| | 48 hrs | 875 | — | — | — |
| | | — | 175 | — | — |
| | | 875 | 12 | 1.07 | 1:0.0137 |
| | | 875 | 6 | 1.03 | 1:0.0069 |
| S. aureus ATCC #6538 | 24 hrs | 1100 | — | — | — |
| | | — | 30 | — | — |
| | | 200 | 15 | 0.68 | 1:0.0750 |
| | | 300 | 15 | 0.77 | 1:0.0500 |
| | | 425 | 15 | 0.89 | 1:0.0353 |
| | | 525 | 15 | 0.98 | 1:0.0286 |
| | | 650 | 15 | 1.09 | 1:0.0231 |
| | | 875 | 7.5 | 1.05 | 1:0.0086 |
| | | 875 | 3 | 0.90 | 1:0.0034 |
| | | 1100 | 3 | 1.1 | 1:0.0027 |
| | | 1100 | 2 | 1.07 | 1:0.0018 |
| | | 1100 | 1 | 1.03 | 1:0.0009 |
| | 48 hrs | 1100 | — | — | — |
| | | — | 60 | — | — |
| | | 200 | 15 | 0.43 | 1:0.0750 |
| | | 300 | 15 | 0.52 | 1:0.0500 |
| | | 425 | 15 | 0.64 | 1:0.0353 |
| | | 525 | 15 | 0.73 | 1:0.0286 |
| | | 650 | 15 | 0.84 | 1:0.0231 |
| | | 875 | 15 | 1.05 | 1:0.0171 |
| | | 875 | 7.5 | 0.92 | 1:0.0086 |
| | | 1100 | 7.5 | 1.13 | 1:0.0068 |
| | | 875 | 3 | 0.85 | 1:0.0034 |
| | | 1100 | 3 | 1.05 | 1:0.0027 |
| | | 1100 | 2 | 1.03 | 1:0.0018 |
| | | 1100 | 1 | 1.02 | 1:0.0009 |

Ca—ppm AI of Propiconazole (1-[[2-(2,4-dichlorophenyl)-4-propyl-1,3-dioxolan-2-yl]methyl]-1H-1,2,4-triazole)
Cb—ppm AI of MBIT(N-methyl-1,2-benzisothiazolin-3-one
Ratio: Ca:Cb

TABLE 6

| Test Organisms | Contact Time | Ca | Cb | S.I. | Ca:Cb |
|---|---|---|---|---|---|
| A. niger ATCC #16404 | 3 days | 4.25 | — | — | — |
| | | — | 37.5 | — | — |
| | | 1.1 | 18.8 | 0.76 | 1:17.0909 |
| | | 2 | 18.8 | 0.97 | 1:9.4000 |
| | 7 days | 11 | — | — | — |
| | | — | 150 | — | — |
| | | 11 | 2.4 | 1.02 | 1:0.2182 |
| | | 11 | 1.2 | 1.01 | 1:0.1091 |
| C. albicans ATCC #10231 | 48 hrs | 110 | — | — | — |
| | | — | 30 | — | — |
| | | 42.5 | 15 | 0.89 | 1:0.3529 |
| | | 52.5 | 15 | 0.98 | 1:0.2857 |
| | | 65 | 15 | 1.09 | 1:0.2308 |
| | | 87.5 | 7.5 | 1.05 | 1:0.0857 |
| | | 110 | 1.86 | 1.06 | 1:0.0169 |
| | | 110 | 0.94 | 1.03 | 1:0.0085 |
| | 72 hrs | 110 | — | — | — |
| | | — | 30 | — | — |
| | | 42.5 | 15 | 0.89 | 1:0.3529 |
| | | 52.5 | 15 | 0.98 | 1:0.2857 |
| | | 65 | 15 | 1.09 | 1:0.2308 |
| | | 87.5 | 7.5 | 1.05 | 1:0.0857 |
| | | 110 | 1.86 | 1.06 | 1:0.0169 |
| | | 110 | 0.94 | 1.03 | 1:0.0085 |
| Ps. aeruginosa ATCC #9027 | 24 hrs | 875 | — | — | — |
| | | — | 100 | — | — |
| | | 650 | 25 | 0.99 | 1:0.0385 |
| | | 875 | 6 | 1.06 | 1:0.0069 |
| | 48 hrs | 1100 | — | — | — |
| | | — | 175 | — | — |
| | | 875 | 50 | 1.08 | 1:0.0571 |
| | | 875 | 25 | 0.94 | 1:0.0286 |
| | | 1100 | 25 | 1.14 | 1:0.0227 |
| | | 1100 | 12 | 1.07 | 1:0.0109 |
| | | 1100 | 6 | 1.03 | 1:0.0055 |
| S. aureus ATCC #6538 | 24 hrs | 300 | — | — | — |
| | | — | 30 | — | — |
| | | 87.5 | 15 | 0.79 | 1:0.1714 |
| | | 110 | 15 | 0.87 | 1:0.1364 |
| | | 200 | 15 | 1.17 | 1:0.0750 |
| | | 200 | 7.5 | 0.92 | 1:0.0375 |
| | | 300 | 7.5 | 1.25 | 1:0.0250 |
| | | 200 | 3 | 0.77 | 1:0.0150 |
| | | 200 | 2 | 0.73 | 1:0.0100 |
| | | 300 | 2 | 1.07 | 1:0.0067 |
| | | 200 | 1 | 0.70 | 1:0.0050 |
| | | 300 | 1 | 1.03 | 1:0.0033 |
| | 48 hrs | 425 | — | — | — |
| | | — | 60 | — | — |
| | | 0.65 | 30 | 0.50 | 1:46.1538 |
| | | 2 | 30 | 0.50 | 1:15.0000 |
| | | 4.25 | 30 | 0.51 | 1:7.0588 |
| | | 6.5 | 30 | 0.52 | 1:4.6154 |
| | | 11 | 30 | 0.53 | 1:2.7273 |
| | | 20 | 30 | 0.55 | 1:1.5000 |
| | | 30 | 30 | 0.57 | 1:1.0000 |
| | | 42.5 | 30 | 0.60 | 1:0.7059 |
| | | 52.5 | 30 | 0.62 | 1:0.5714 |
| | | 65 | 30 | 0.65 | 1:0.4615 |
| | | 87.5 | 30 | 0.71 | 1:0.3429 |
| | | 110 | 30 | 0.76 | 1:0.2727 |
| | | 200 | 30 | 0.97 | 1:0.1500 |
| | | 300 | 30 | 1.21 | 1:0.1000 |
| | | 87.5 | 15 | 0.46 | 1:0.1714 |
| | | 110 | 15 | 0.51 | 1:0.1364 |
| | | 200 | 15 | 0.72 | 1:0.0750 |
| | | 300 | 15 | 0.96 | 1:0.0500 |
| | | 425 | 15 | 1.25 | 1:0.0353 |
| | | 200 | 7.5 | 0.6 | 1:0.0375 |
| | | 300 | 7.5 | 0.83 | 1:0.0250 |
| | | 425 | 7.5 | 1.13 | 1:0.0176 |
| | | 200 | 3 | 0.52 | 1:0.0150 |
| | | 300 | 3 | 0.76 | 1:0.0100 |
| | | 425 | 3 | 1.05 | 1:0.0071 |
| | | 200 | 2 | 0.5 | 1:0.0100 |
| | | 300 | 2 | 0.74 | 1:0.0067 |
| | | 425 | 2 | 1.03 | 1:0.0047 |

TABLE 6-continued

| Test Organisms | Contact Time | Ca | Cb | S.I. | Ca:Cb |
|---|---|---|---|---|---|
| | | 200 | 1 | 0.49 | 1:0.0050 |
| | | 300 | 1 | 0.72 | 1:0.0033 |
| | | 425 | 1 | 1.02 | 1:0.0024 |

Ca—ppm AI of Tebuconazole (alpha-[2-(4-chlorophenyl)ethyl]-alpha-(1,1-dimethylethyl)-1H-1,2,4-triazole-1-ethanol)
Cb—ppm AI of MBIT (N-methyl-1,2-benzisothiazolin-3-one)
Ratio: Ca:Cb

The invention claimed is:

1. A microbicidal composition comprising:
(a) N-methyl-1,2-benzisothiazolin-3-one; and
(b) tebuconazole; and a ratio of tebuconazole to N-methyl-1,2-benzisothiazolin-3-one is from 1:0.0033 to 1:0.0375 or from 1:0.0750 to 1:46; wherein the microbicidal composition is synergistic.

* * * * *